United States Patent [19]
Carr et al.

[11] Patent Number: 5,712,460
[45] Date of Patent: Jan. 27, 1998

[54] MULTI-FUNCTION SURGICAL DEVICE CONTROL SYSTEM

[75] Inventors: Raymond A. Carr, Clearwater Beach; David A. Cianciolo, Largo, both of Fla.

[73] Assignee: Linvatec Corporation, Largo, Fla.

[21] Appl. No.: 714,913

[22] Filed: Sep. 17, 1996

Related U.S. Application Data

[63] Continuation of Ser. No. 276,979, Jul. 19, 1994, abandoned.
[51] Int. Cl.$^6$ .............................. H01C 10/10; H01H 3/14
[52] U.S. Cl. .................... 200/86.5; 338/108; 338/153
[58] Field of Search .............................. 200/4, 5 R, 5 A, 200/6 R, 6 A, 16 R, 16 A, 16 B, 16 C, 16 D, 17 R, 18, 61.54, 85 R, 86 R, 86.5, 61.89, 512–517; 338/2, 108, 110, 153

[56] References Cited

U.S. PATENT DOCUMENTS

| | | | |
|---|---|---|---|
| 3,125,739 | 3/1964 | Deibel et al. | |
| 3,911,241 | 10/1975 | Jarrard | 200/157 |
| 4,055,735 | 10/1977 | Eachus et al. | 200/5 A |
| 4,121,488 | 10/1978 | Akiyama | |
| 4,163,204 | 7/1979 | Sado et al. | |
| 4,168,707 | 9/1979 | Douvas et al. | |
| 4,200,106 | 4/1980 | Douvas et al. | |
| 4,258,100 | 3/1981 | Fujitani et al. | |
| 4,639,710 | 1/1987 | McMillan et al. | |
| 4,650,934 | 3/1987 | Burke | 200/5 R |
| 4,705,038 | 11/1987 | Sjostrom et al. | |
| 4,867,155 | 9/1989 | Isaacson | |
| 4,916,262 | 4/1990 | Lungels-Butler et al. | 200/518 |
| 4,995,877 | 2/1991 | Ams et al. | |
| 5,077,506 | 12/1991 | Krause | |
| 5,251,636 | 10/1993 | Neuman | |
| 5,324,900 | 6/1994 | Gonser et al. | 200/86.5 |
| 5,340,953 | 8/1994 | Krebs et al. | 200/86.5 |
| 5,351,676 | 10/1994 | Putman | 128/4 |
| 5,461,355 | 10/1995 | Schemansky et al. | 338/108 |

OTHER PUBLICATIONS

IntraArc 9963 Arthroscopy Power System, Concept Arthroscopy Products Catalog 1992 (3 pages).
Operating the Instrument, 9963 IntraArc Drive System (2 pages).
V. Mueller Endoscopy, PowerCut Gold Surgical System, 1992 (4 pages).
Force Sensing Resistors, Unlock the Power of Touch, Interlink Electronics (6 pages).
The Quadracut ACL/Shaver System, Stryker Endoscopy, 1993 (4 pages).
The PS3500EP Shaver System, Unlocking the Future of Arthroscopic Surgery, Smith +Nephew Dyonics, 1992 (4 pages).
The FSR Front Panel, Interlink Electronics (2 pages).
The FSR Rugged Keypad, Interlink Electronics (2 pages).
Suggested Interfaces, TechNotes, Interlink Electronics, Rev. Sep. 1990 (31 pages).
FSR Integration Guide and Standard Parts Catalog, Interlink Electronics, Rev. Jul. 1992 (18 pages).

*Primary Examiner*—Michael L. Gellner
*Assistant Examiner*—Michael A. Friedhofer
*Attorney, Agent, or Firm*—Gene Warzecha

[57] ABSTRACT

A multi-function control system to control a variety of operations associated with a powered surgical device such as an arthroscopic surgical shaver. The system has an ergonomically designed foot switch which has a plurality of discrete force sensitive transducers arranged in an arcuate pattern. The transducers have no moving parts and have a force sensitive element which produces a variable output which is a function of the force applied by a user. The foot switch is used in conjunction with a control console which enables a user to adjust the force sensitivity threshold of the transducers. The foot switch additionally has physically discrete and tactilely sensible areas enabling a user to activate selected functions with a minimal amount of foot movement.

10 Claims, 11 Drawing Sheets

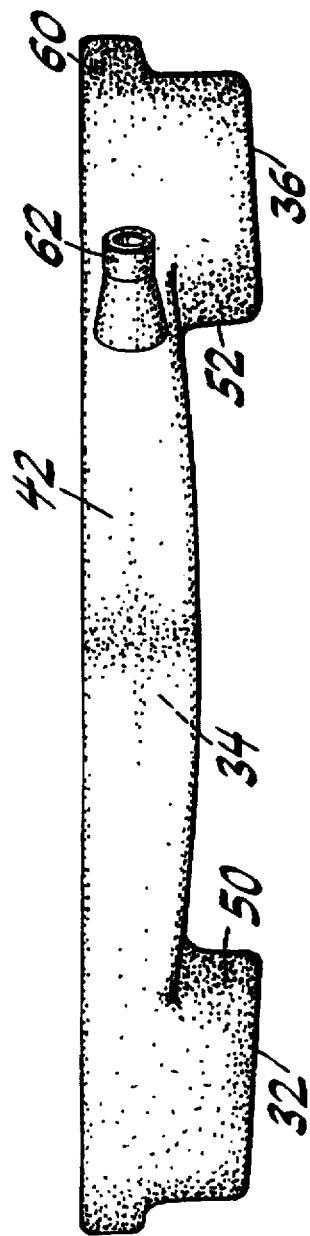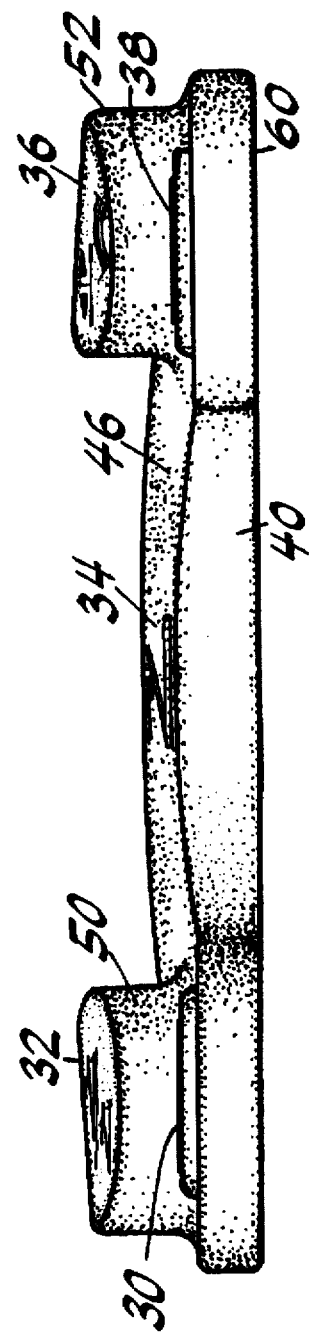

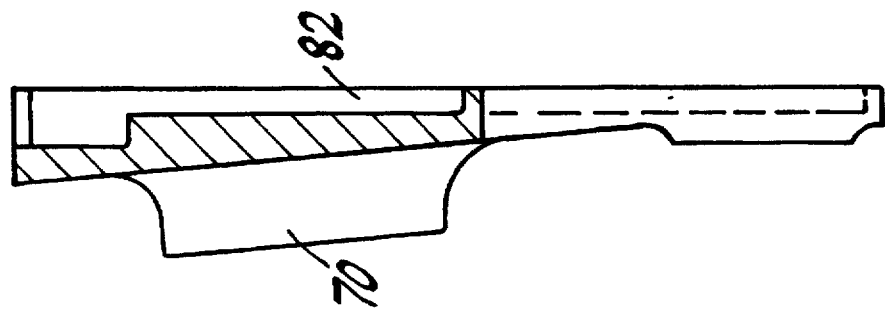
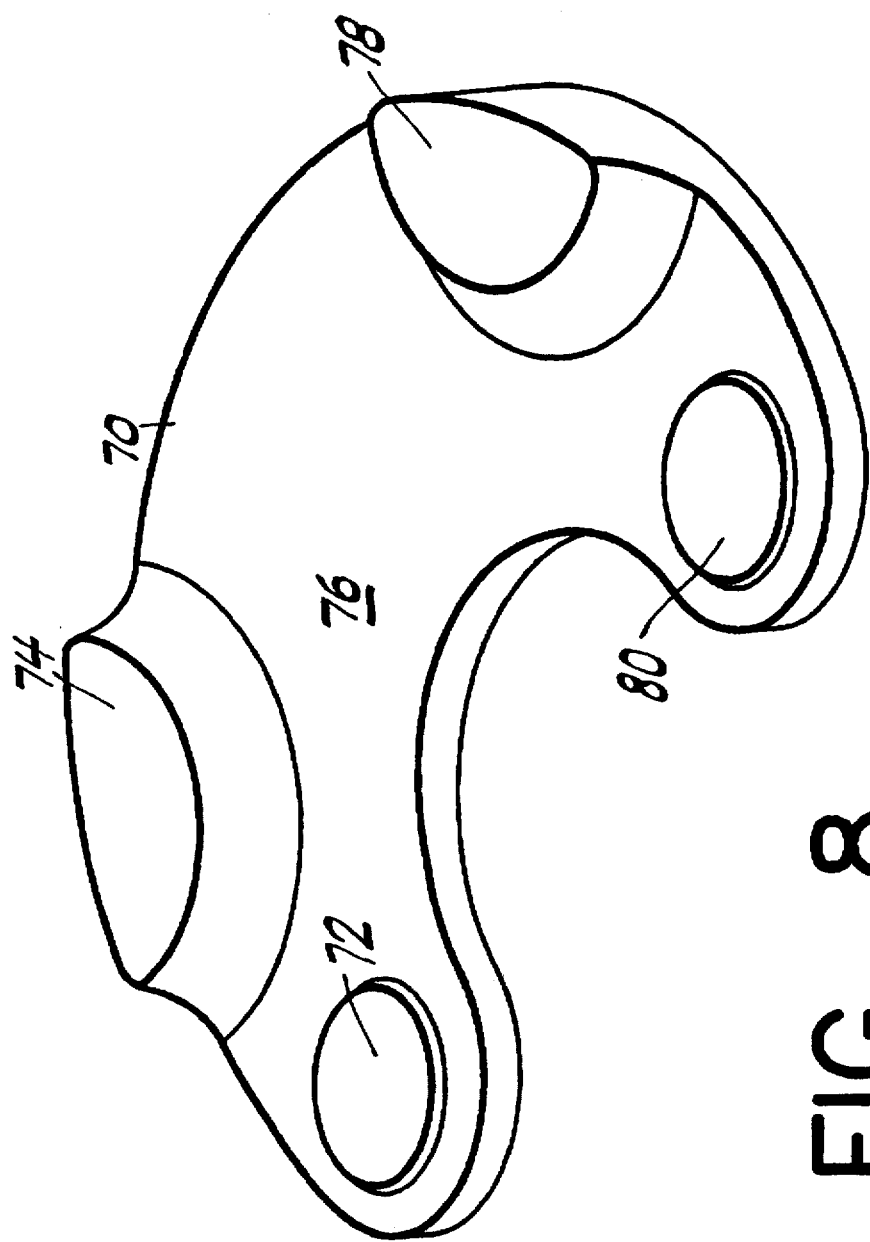

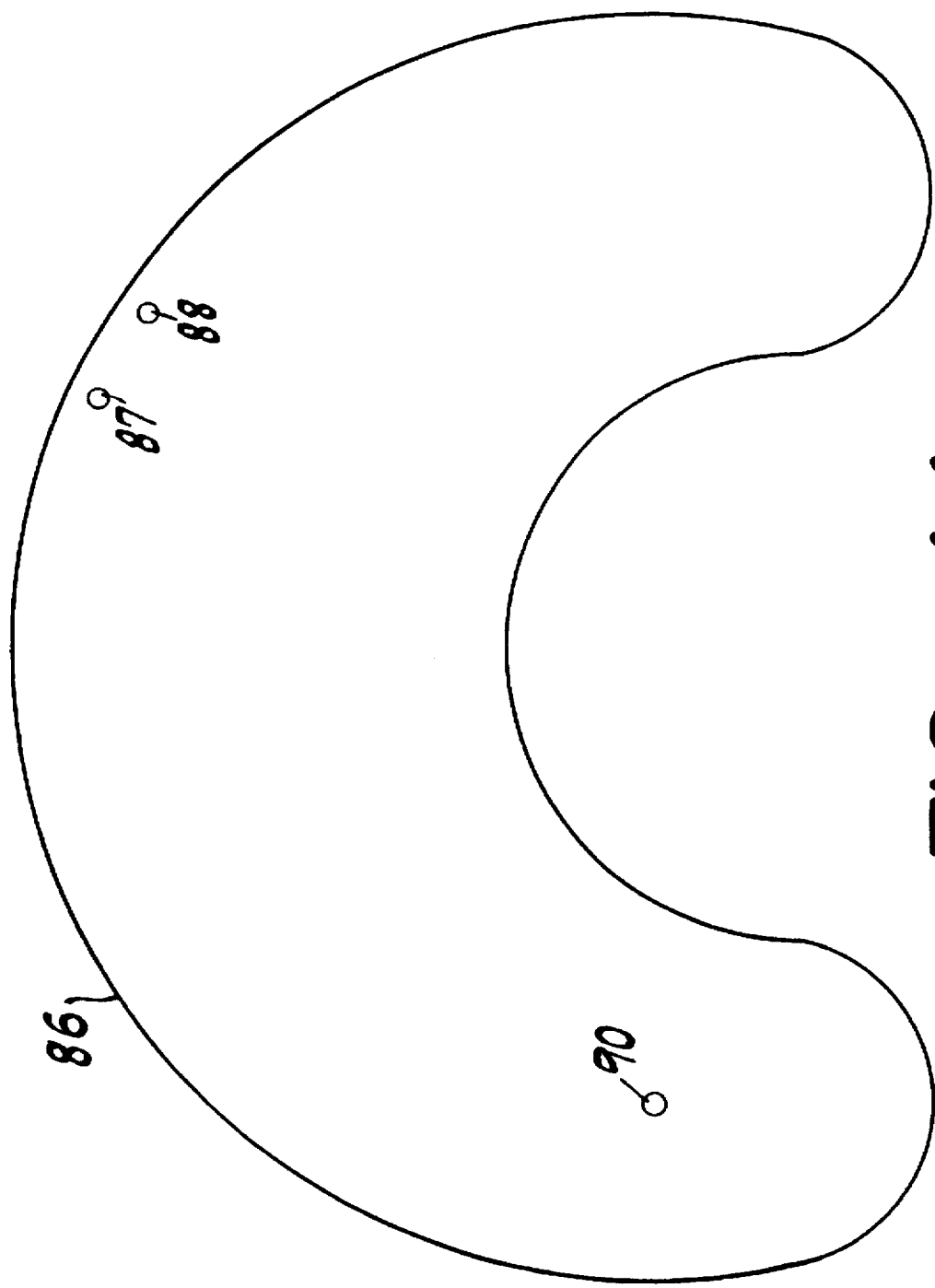

MULTI-FUNCTION SURGICAL DEVICE CONTROL SYSTEM

This is a continuation application Ser. No. 08/276,979, filed Jul. 19, 1994 and abandoned Nov. 6, 1996.

BACKGROUND OF THE INVENTION

1. Field of the Invention

The invention relates to a control mechanism for selecting and operating various functions performed by a surgical device control system. More particularly, the invention relates to a foot switch and method for controlling a powered surgical device such as a drive system for powering surgical cutting instruments.

2. Description of the Prior Art

Surgical drive systems are used for powering and controlling a variety of surgical cutting instruments. With respect to arthroscopic or endoscopic surgical procedures, surgical drive systems are generally controlled by the surgeon via hand or foot control devices. This invention pertains primarily to those devices which are operated by foot switches having a plurality of functions.

The foot switch and method of the present invention will be described in the context of a drive system for use in controlling a rotatable surgical shaver although it will be understood that the invention is applicable to other powered surgical devices such as irrigation/aspiration pumps, etc. A rotatable surgical shaver comprises a handpiece having an elongated, inner tubular member situated within a fixed elongated outer tubular member. The proximal ends of both inner and outer members are attached to a handpiece with the proximal end of the outer tubular member being fixed relative to the handpiece and the proximal end of the inner tubular member being rotatable by a motor situated within the handpiece. The distal end of the inner member is provided with a cutting or abrading element and the distal end of the outer member is provided with a window or opening through which the cutting element of the inner member may operate. In certain embodiments, the inner and outer member assembly is generally known as a shaver blade wherein the cutting element of the inner member may cooperate with the window of the outer member to achieve a shearing-type cutting action. In other embodiments the assembly is known as a burr wherein the inner member abrades the tissue through the opening in the outer. The term "cut"refers to all types of cutting or abrading. The cut tissue is aspirated away from the work site through the lumen of the inner member. The rotational speed of the inner member relative to the outer member as well as the direction of rotation and the acceleration of the inner member are parameters which are controllable by surgeons in the use of the devices.

Depending upon the particular surgical procedure, the aforementioned surgical instruments may be used by a surgeon with either a hand or foot control, with the surgeon either sitting or standing. Hand control devices incorporate control switches on the handpiece manipulated by the surgeon and foot control devices incorporate the control switch within a foot switch. It has been found desirable to have a foot switch controller for controlling various functions of the surgical drive system. For example, known foot switch controllers control the direction of rotation of the inner member relative to the outer member (i.e. forward or reverse), the mode of rotation (i.e. single direction of rotation or oscillation). In some instances, the speed of rotation is able to be increased or decreased by adjusting the degree to which a foot switch is depressed.

Prior art foot switches are generally flat rectilinear structures having a plurality of foot actuated levers which in turn move microswitches or activate Hall-effect switches in order to produce either a simple on/off signal or a variable signal, the signals being then used by a control console to produce the desired function in the instrument. These prior art foot switches are able to operate with only one degree of sensitivity. That is, once the switch is designed and manufactured a user may operate the switch to achieve a desired function by depressing a selected button or lever with a predetermined amount of force, the amount of force being determined by the built-in springs, pads and other elements of the foot switch. Thus, prior art foot switches do not enable any variability of the sensitivity of the various switches on the foot switch to accommodate different situations. For example, a surgeon operating a foot switch in a sitting position may desire to depress the foot switch with a different amount of force than if the same foot switch is operated in a standing position.

Moreover, known foot switches, because of their rectilinear construction are unable to easily provide for the control of a large number of functions. Generally, the four corners of a rectilinear switch are the most easily identifiable areas for a surgeon to control especially given the fact that the foot switches are generally used in a tactile mode since the surgeon is unable to directly view the foot switch during use.

Accordingly, it is an object of this invention to produce a foot switch controller for a surgical drive system in which the controller provides a tactile element to the surgeon during use.

It is another object of this invention to produce a foot switch for a surgical drive system in which the various controls provided by the foot switch are easily located by a surgeon without an undue amount of movement of the surgeon's foot during a surgical procedure.

It is yet another object of this invention to provide a drive system having a foot switch in which the sensitivity of the foot switch to pressure may be adjusted to accommodate personal preferences and/or varying operational positions.

It is yet another object of this invention to provide a drive system having a foot switch with no moving parts.

It is yet another object of this invention to provide a drive system having a foot switch which may be controlled in a programmable manner.

It is still another object of this invention to provide a surgical drive system capable of communicating with associated surgical systems such as an irrigation/aspiration system.

It is also an object of this invention to produce an ergonomically designed foot switch to facilitate its use during the performance of an endoscopic surgical procedure.

SUMMARY OF THE INVENTION

These and other objects of this invention are achieved by the preferred embodiment disclosed herein which is a foot switch for an endoscopic cutting apparatus comprising a hollow, elongated rotatable inner shaft adapted to rotate within an elongated outer shaft, the foot switch comprising a C-shaped base plate, a C-shaped printed circuit membrane affixed to one side of the base plate and a plurality of force sensitive resistors operatively connected to the printed circuit membrane. The force sensitive resistors are arranged in a substantially arcuate pattern on the printed circuit membrane. A flexible C-shaped molded cover is adapted to receive the base plate and printed circuit membrane. The cover comprises predetermined function-activating areas in alignment with the force sensitive resistors, the predetermined areas being sufficiently flexible to enable selected ones to be depressed to apply force to a corresponding underlying force sensitive resistor to activate a predetermined function associated therewith.

The invention also comprises a method for adjusting the sensitivity of a control switch for controlling the speed of a surgical cutting instrument. The method comprises the steps of providing a switch having a force sensitive resistor for controlling a predetermined parameter of the surgical cutting instrument and monitoring a characteristic of the force sensitive resistor, the characteristic being a function of the pressure applied to the force sensitive resistor. A sensitivity control means responsive to this characteristic is then used for producing a signal representative of a predetermined force sensitivity and the value of the signal at which the force sensitive resistor becomes operational is adjusted.

Another invention disclosed herein comprises a method of controlling the speed of rotation of a rotatable surgical shaver having a rotatable elongated inner member within a fixed elongated outer member, the outer member having a distal cutting window and the inner member having a cutting means which cyclically covers the cutting window. The method comprises the steps of adjusting the speed of rotation of the inner member to a predetermined slow rate and monitoring the size of said window opening at the distal end of the shaver. The method further comprises stopping the rotation of the inner member at a predetermined point to thereby create a predetermined size window opening which may be made as large as possible to facilitate aspiration of fluid from the work site.

BRIEF DESCRIPTION OF THE DRAWINGS

FIG. 5 is a top plan view of FIG. 2.

FIG. 6 is a bottom plan view of FIG. 2.

FIG. 8 is a front perspective view of a foam insert molded to conform to the interior of the covering of the foot switch of FIG. 1.

FIG. 10 is a cross-sectional view of FIG. 9 taken along the lines 10—10.

FIG. 11 is a top plan view of the base plate which forms a part of the invention.

DESCRIPTION OF THE PREFERRED EMBODIMENT

Figure 1:
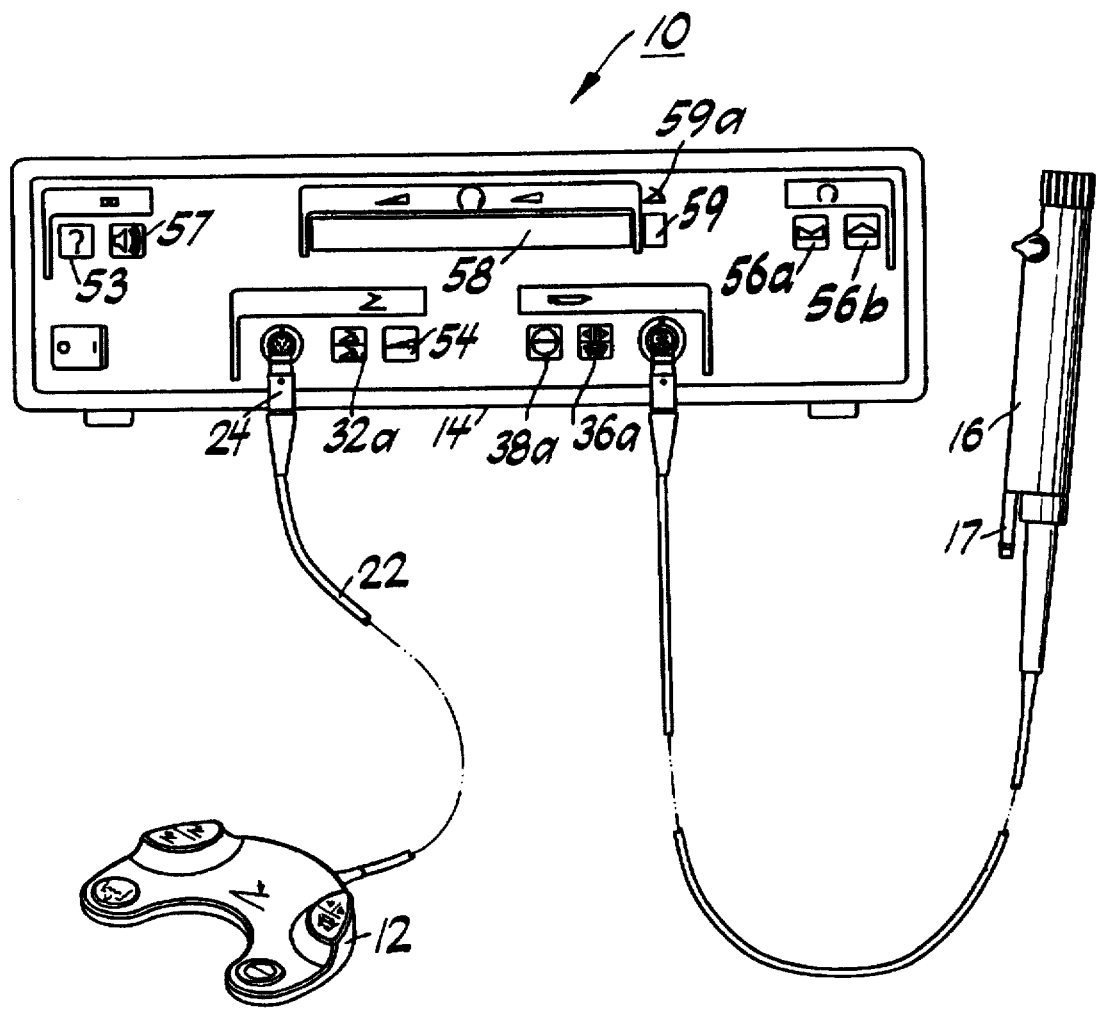
FIG. 1 is a schematic view of a surgical shaver drive system showing a front perspective view of a foot switch and a surgical shaver control console, constructed in accordance with the principles of this invention, and a handpiece.

Referring now to FIG. 1, there is shown a diagrammatic representation of a surgical cutting system 10 designed primarily for controlling rotatable, motor driven arthroscopic cutting blades. The invention is equally applicable to any endoscopic motor driven cutting type device. System 10 comprises foot switch 12, console 14 and handpiece 16. Handpiece 16 forms no part of the present invention and is shown merely for explanatory purposes. A prior art drive system and a handpiece similar to handpiece 16 are described in U.S. Pat. No. 5,269,794 (Rexroth) assigned to the assignee hereof and incorporated by reference herein. Handpiece 16 is designed to selectively receive arthroscopic cutting instruments comprising a rotatable elongated inner member situated within a fixed elongated outer member. Cutting edges at the distal end of the inner member serve to resect or abrade tissue during endoscopic surgical procedures, the debris being removed from the surgical site through the lumen of the inner member via an aspirating suction port 17 as will be understood by those skilled in the art.

The present invention is embodied in foot switch 12 and in certain portions of console 14 which affect the manner in which the blades attached to handpiece 16 are operated during a surgical procedure. As used herein, the term "blades" means any cutting device operated by system 10 including rotatable blades, burrs, etc. Console 14 incorporates several control buttons on its front panel, the purpose of which will be discussed below in conjunction with foot switch controls.

Foot switch 12, shown in greater detail in FIGS. 2 through 13, comprises a flat arcuate body 20 joined via an electrical cable 22 to connector 24 which is adapted to mate to a corresponding socket in the front of console 14. Body 20 comprises a generally C-shaped structure having a plurality of unique force sensitive switches arranged in an arcuate pattern about a central point 26. In the preferred embodiment, five discrete switch locations 30, 32, 34, 36 and 38 are arranged arcuately around center 26. The arcuate inside and outside edges 40 and 42, respectively, of foot switch body 20 need not necessarily be semicircular or concentric relative to point 26 and the precise shape of these edges and of the overall foot switch may be changed without departing from the spirit of the invention.

Foot switch 12 has been ergonomically designed to enable a user to activate a plurality of functions with minimal effort. As will be noted from FIGS. 3 through 6, foot switch body 20 is inclined relative to center 26 and discrete switch areas 32 and 36 are raised relative to top surface 46 of body 20. The raised aspect of switch areas 32 and 36 defines peripheral surfaces 50 and 52, respectively, surrounding these switch areas and facilitating their location by a user's foot without the user having to actually look at the foot switch. Additionally, as will be understood below, the operational characteristics of foot switch 12 are adjustable to suit a user's preference. This feature is particularly useful in adapting the foot switch so a user may use it while either standing or sitting.

In the preferred embodiment, the switches at the discrete switch locations are associated with different modes of operation of handpiece 16 and some of them are wired in parallel with switches on the front panel of console 14 (and in parallel with control buttons on the handpiece in some cases, not shown). For example, switch 30 is an on/off "vacuum actuation" switch for controlling an associated irrigation/aspiration system (not shown) to indicate whether or not a vacuum should be applied to the suction port 17 attached to handpiece 16. Switch 32 is the "Variable/Normal" switch which controls the type of rotation of the blades attached to handpiece 16 and operates in conjunction with the "Blade Activate" switch 34 which controls the rotational speed of the inner member within the outer member. The rotational speed may be either varied within a certain range (i.e. variable) or fixed at a set rate (i.e. normal). In the "variable" mode, switch 34, when depressed and held, varies the rate of blade rotation (within the particular predetermined limits for each blade) depending upon the amount of pressure applied. In the "normal"mode, switch 34 merely acts as an on/off switch. Switch 36 is the "Reverse/Forward/Oscillate" switch which controls the direction of rotation of the blades and also can place the blades in an oscillating mode. Switch 38 is the "Aspirate Mode" switch which, when depressed and held, rotates the inner blade at a slow rate of speed (e.g. 60 revolutions per minute) so that a user may, under arthroscopic viewing of the cutting window, stop the inner blade at a precise location to achieve a window opening of desired size through which liquid and/or debris may be aspirated by an associated irrigation/aspiration system (not shown). While the size of the opening is monitored visually in the preferred embodiment, alternative ways of doing this could include automatic means such as monitoring an electrical signal representative of the blade portion and using this to stop the blade at a predetermined position. Switches 32, 36 and 38 are wired in parallel with switches 32a, 36a and 38a on console 14, thus enabling the "variable/normal ", "forward/reverse/oscillate "and "aspirate"functions to be controlled from either location.

As will be understood below, the sensitivity of each switch on foot switch 12 is adjustable and, therefore, the force with which the switches may be activated may be adjusted to a user's preference. Additionally, each switch activation may be accompanied, if desired, by an audio prompt to audibly identify for the user which function has been selected. For example, the words "aspirate", "forward", "reverse", "oscillate", "variable", "normal"and "vacuum" could be programmed to occur when the associated switch is depressed.

Referring to FIG. 1, console 14 includes a foot switch sensitivity button 54 which, by cycling through discrete settings (e.g. low, medium, high) allows a user to adjust the pressure required to activate functions via the foot switch (as will be explained below). Speed control buttons 56a and b, respectively, allow the user to decrease and increase the blade speed in RPM (revolutions per minute) which is displayed on display 58. Buttons 56a and b each have two functions: in the Normal mode of operation the blade speed is controlled, and in the Program Setup Mode, the display is cycled through a menu selection. Indicator 59 shows an arrow pointing up to the variable foot switch icon 59a when the system is in the variable speed mode. "Audio " button 57 enables a user to select the audio level or turn off the audio prompts and "help"button 53 provides the user with a brief explanation at various stages in the menu.

Figure 7:
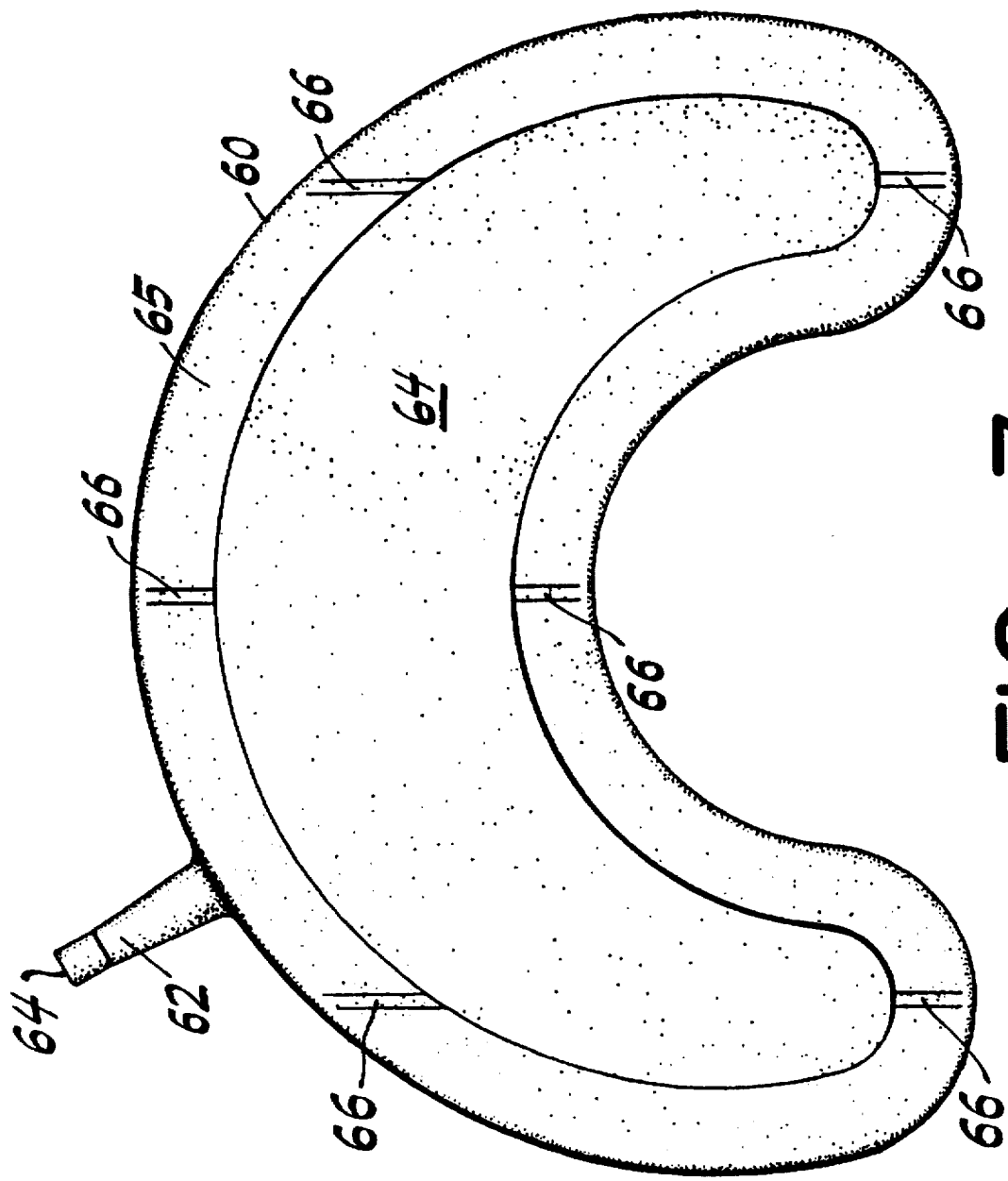
FIG. 7 is a rear elevation view of FIG. 2.

Foot switch body 20 comprises a unitary, molded hollow shell 60 which is formed with a minimal number of openings in order to facilitate the production of a waterproof foot switch suitable for use in an arthroscopic surgical environment. While many polymeric, water-impermeable materials may be suitable, in the preferred embodiment, molded shell 60 is formed of a resilient polyvinylchloride material having a cable strain relief extension 62 with an opening 64 for receiving cable 22. The only other opening in shell 60 is a relatively large arcuately shaped area 64 along the rear surface of shell 60 which facilitates the insertion of the internal components of the foot switch as will be understood below. Opening 64 is bounded by a closed peripheral edge 65. As best seen in FIG. 7, a plurality of fluid passing channels 66 are formed in the outer surface of peripheral edge 65 on the bottom or rear surface of the shell surrounding open area 64. Channels 66 aid in preventing the foot switch from hydroplaning along a wet surface.

Figure 9:
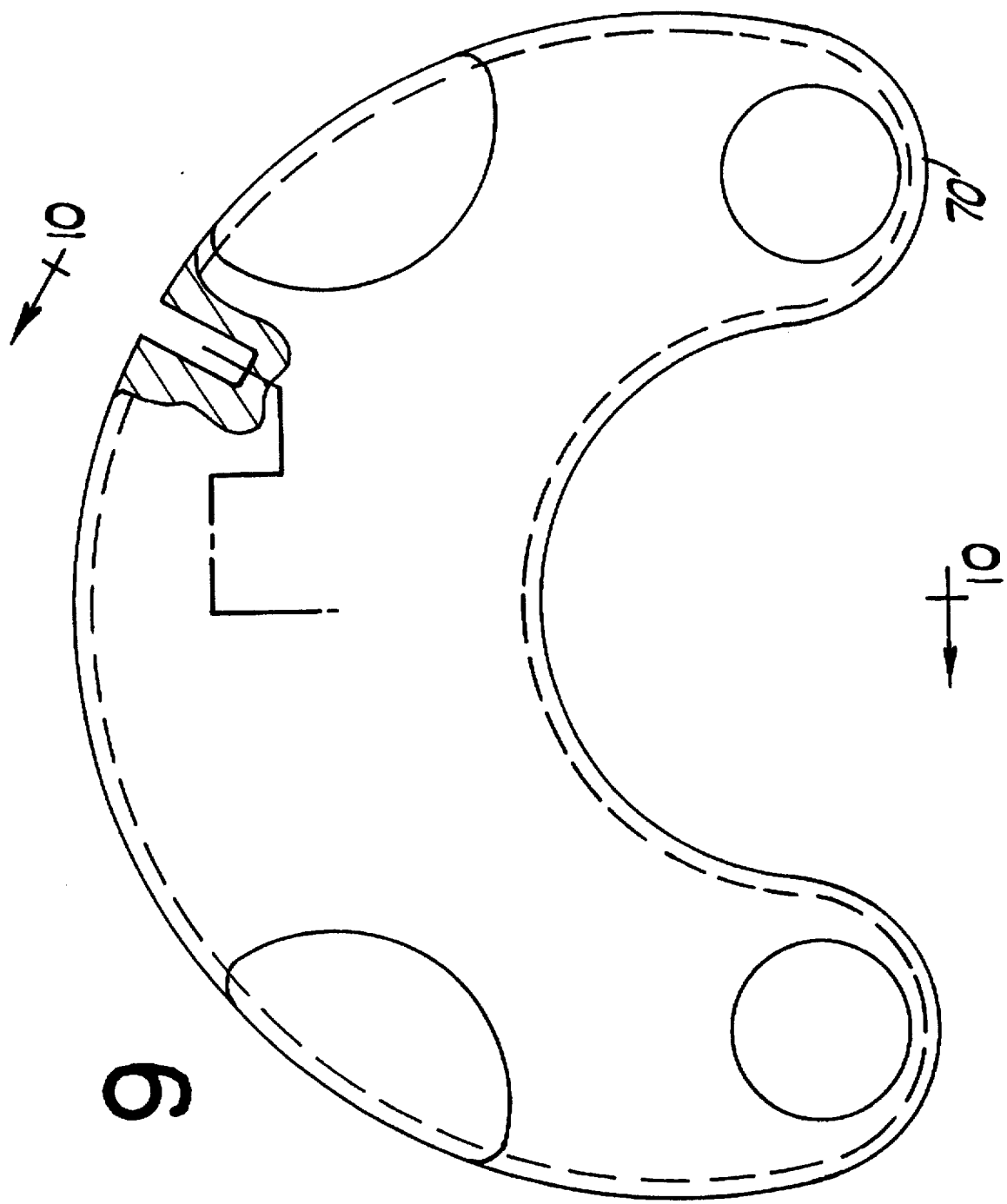
FIG. 9 is a top plan view of the foam insert of FIG. 8 partially in cross-section.

The majority of the hollow interior of shell 60 is filled with an elastomeric (e.g. molded polyurethane foam) insert 70 best seen in FIGS. 8 through 10. As shown in FIG. 8, insert 70 is uniquely shaped in areas 70, 72, 74, 76, 78 and 80 to conform to the interior of shell 60 adjacent switch areas 30, 32, 34, 36 and 38, respectively. The elastomeric filler helps to distribute the force as well as to assure some degree of switch activation even if the point of force application varies slightly during use. As best seen in FIGS. 9 and 10, the rear surface of insert 70 is formed with an arcuate recess 82 in order to receive a base plate and cable connection as will be explained below.

Figure 12:
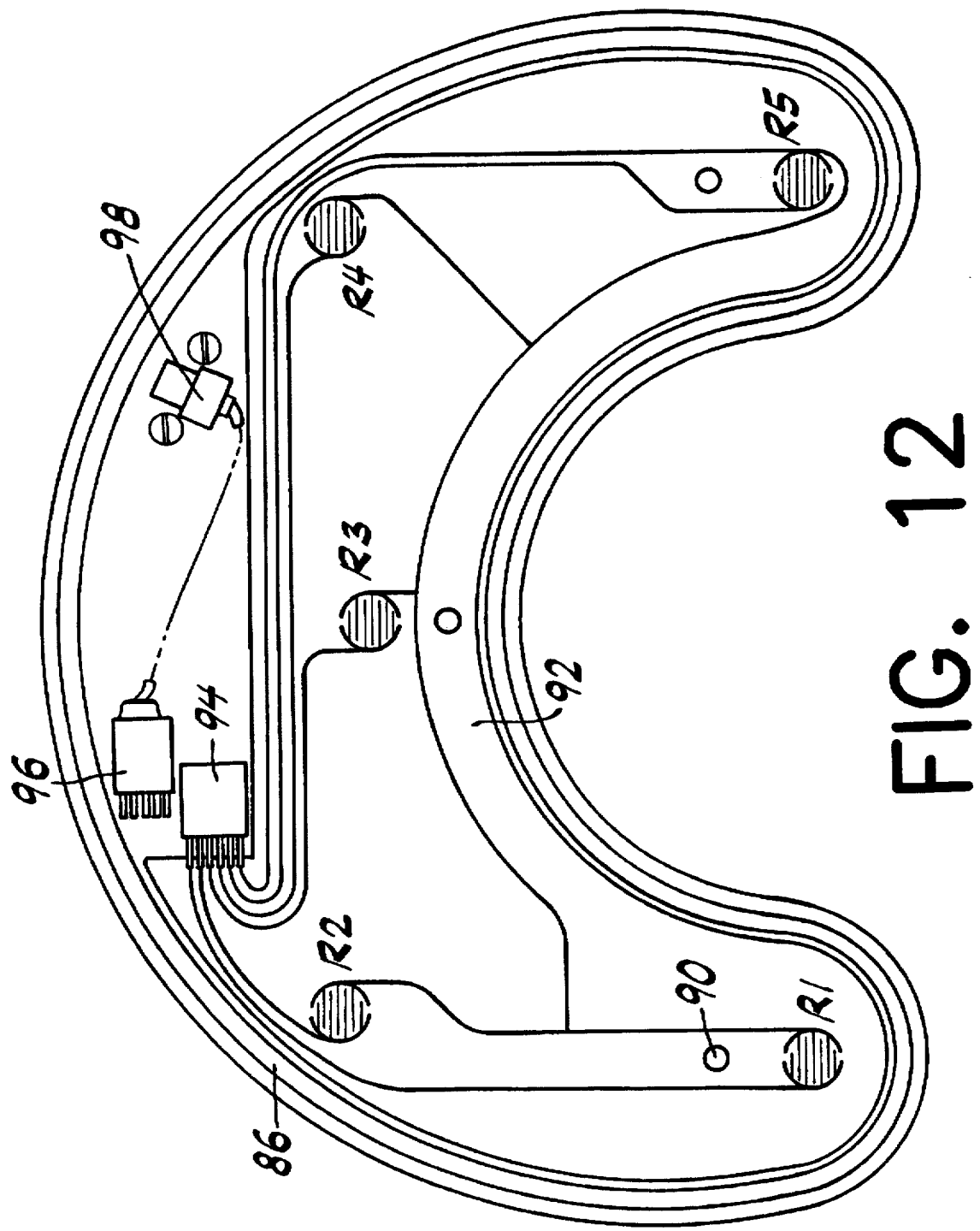
FIG. 12 is a plan view of the printed circuit force sensitive membrane used in the preferred embodiment of the invention disclosed herein.

FIG. 11 shows an arcuate base plate 86 which is another component of foot switch 12. Base plate 86 is provided with a pair of apertures 87 and 88 for retaining a cable connector (98 described below) and a leak-testing aperture 90 for enabling the pressurization of the interior of foot switch 20 during manufacture. The elevated pressure is used to test the seals used to seal openings in the foot switch and, once the test is completed the interior is vented through aperture 90 which is then sealed itself. In the preferred embodiment, base plate 86 is aluminum and provides mechanical support and weight to the foot switch. The base plate may be coated with a suitable material if necessary to enhance the seal between the plate and the peripheral surface around opening 64 of shell 60. As shown in FIG. 12, base plate 86 is adapted to receive on its top surface a printed circuit membrane 92 which contains force sensitive resistors R1, R2, R3, R4 and R5 arranged in a generally arcuate pattern designed to underlie switch areas 30, 32, 34, 36 and 38 respectively. While other suitable force sensitive transducers may be used (e.g. conductive elastomeric materials, etc.) either individually or arranged in a matrix, the force sensitive transducers used in the preferred embodiment are available from Interlink Electronics of Carpinteria, Calif. in the form of resistors and a membrane having two layers of film substrate, one supporting interdigitating conducting electrodes and the other supporting a semiconductive polymer laminated together with a spacer in between. A characteristic of the force sensitive resistor is that an increase in pressure applied to the resistor results in increased shunting of the conductive layer and ultimately a decrease in resistance. The system monitors this varying resistance in order to control the operation of the shaver blades. The various printed conducting paths are terminated at a connector 94 which mates with jumper cable assembly 96 which is in turn connected to cable connector 98.

The term "force sensitive transducer" is used to refer to any device which has no moving parts (such as levers, plates, springs, etc.) and which can produce an output signal which may vary proportionally as a function of the force applied to the device. Conventional on/off mechanical switches are excluded from this definition. Devices such as the aforementioned force sensitive resistors which have a slight movement are included in this definition since no gross or perceptible movement occurs in such devices. Piezoelectric, conductive elastomers and similar devices are also suitable.

Figure 2:
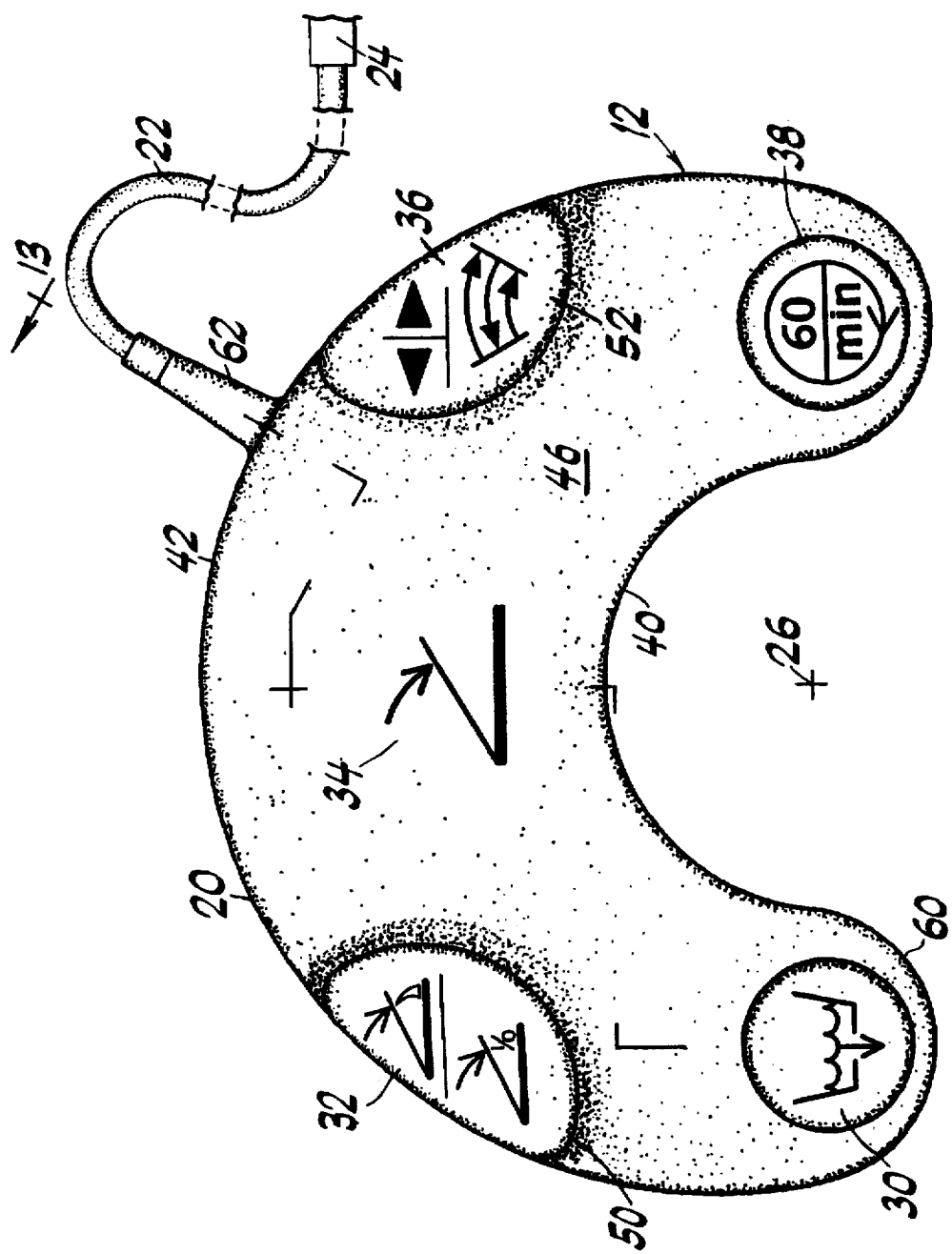
FIG. 2 is a top plan view of the foot switch of FIG. 1.
Figure 3:
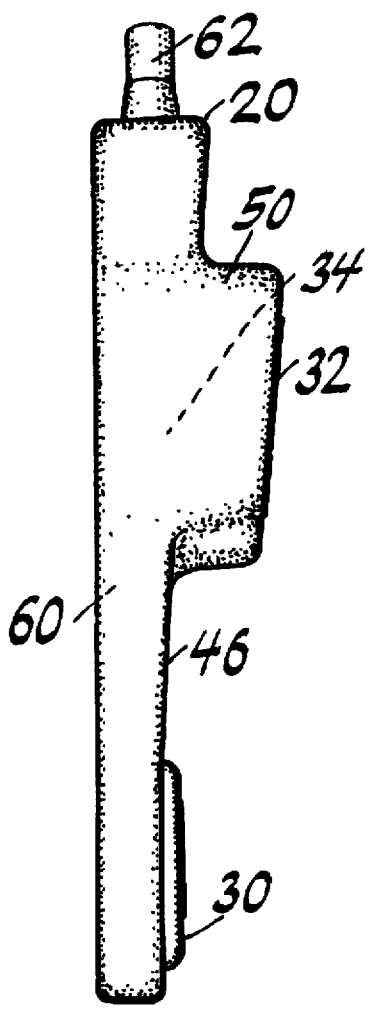
FIG. 3 is a left side elevation view of FIG. 2.
Figure 4:
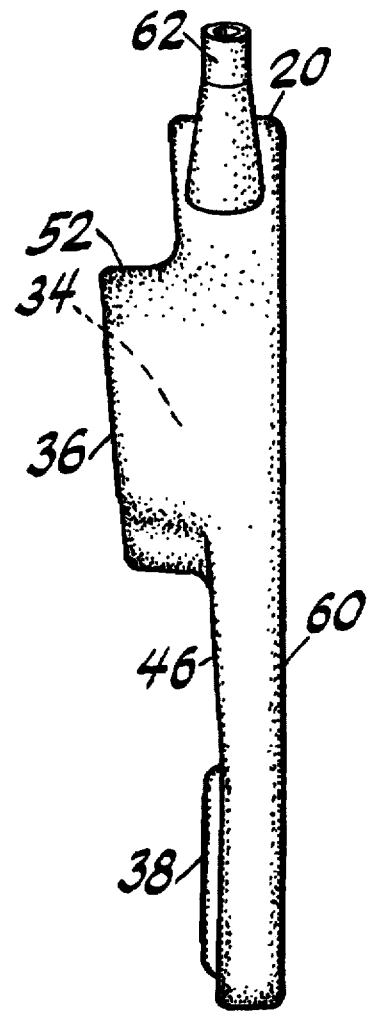
FIG. 4 is a right side elevation view of FIG. 2.
Figure 13:
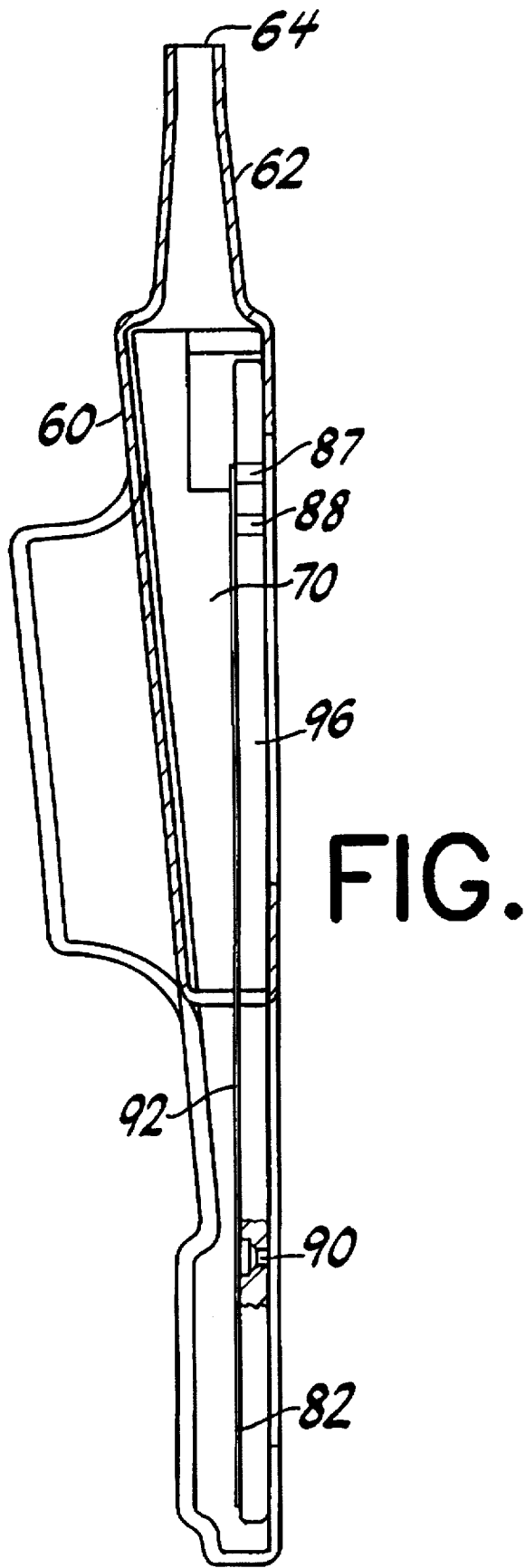
FIG. 13 is a cross-sectional view of FIG. 2 taken along the lines 13—13.

FIG. 13 shows the assembled foot switch as a cross-section of FIG. 2 taken along the lines 13—13. The hollow interior of shell 60 is shown essentially filled with a foam insert 70. The printed circuit membrane 92 and base plate 86 are shown nested into recess 82 in the rear of the foam insert.

Once this assembly is completed, the peripheral edge 65 is sealed with a suitable adhesive sealant and the interior of the unit is leak-tested via aperture 90 which is then also sealed.

Figure 14:
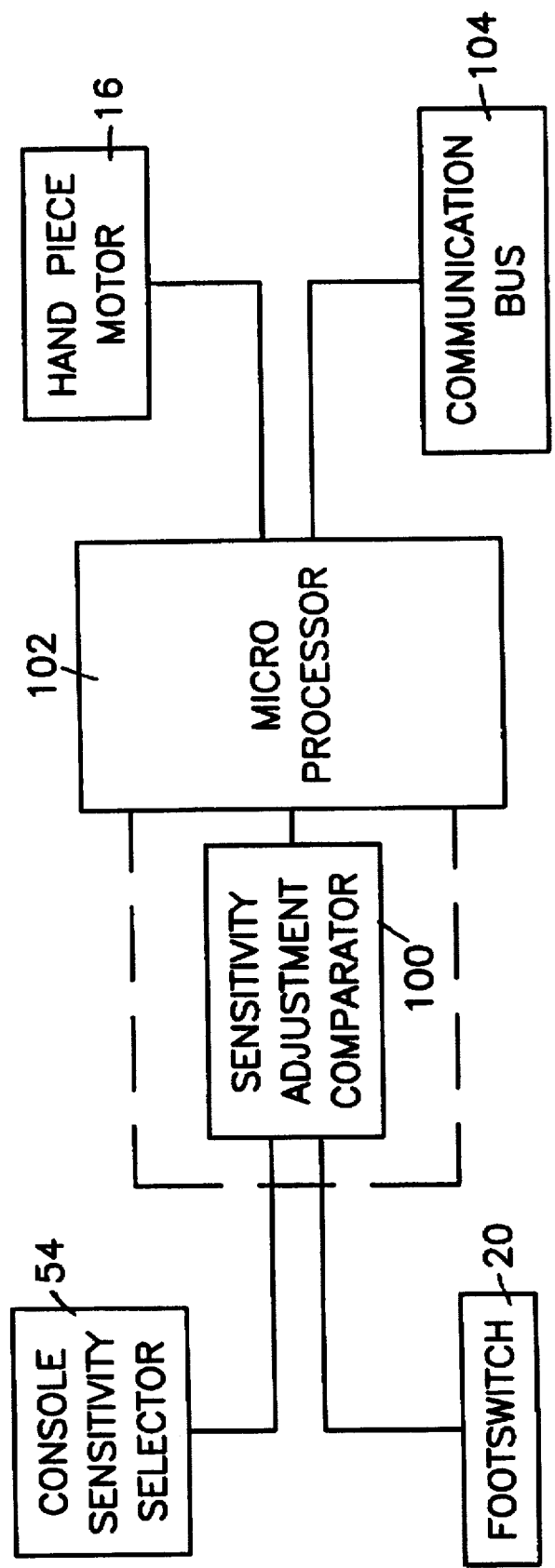
FIG. 14 is a diagrammatic representation of the sensitivity adjustment control system used in the preferred embodiment of the invention.

The actuation thresholds of the various switch functions are easily programmed through the use of force sensitive transducers. This enables a user to adjust the force required to control the various functions depending on personal preference (e.g. the force desired when using the foot switch while seated may be less than when using it while standing). As shown diagrammatically in FIG. 14, the signal outputs of foot switch 12 and console sensitivity selector 54 are provided to a sensitivity adjustment software comparator 100 within microprocessor 102. The output of comparator 100 is, therefore, a function of the threshold selected by the user via sensitivity selector 54 and the force with which the discrete areas of foot switch 12 are depressed. The comparator output signal is provided by microprocessor 102 which ultimately controls handpiece 16 in the manner directed by the foot switch. The microprocessor output can also be provided to a communications bus 104 to control other functions (not shown). For example, if the aspirate mode is selected, not only can the motor be stopped in a desired position but the vacuum applied to the handpiece may be increased by communicating an appropriate signal to an associated integration/aspiration system (not shown). Numerous other functions could be affected by bus 104.

The function of comparator 100 is, in the Normal mode, similar to an on/off switch in that the output of the comparator is a given value when the signal from the force sensitive resistor exceeds a given sensitivity threshold. In the Variable mode, the sensitivity selector button 54 produces discrete ranges (corresponding to, e.g., low, medium and high sensitivity values) and comparator 100 performs a scaling adjustment function. Each sensitivity range is a range of levels with a minimum and maximum value. When the signal from a force sensitive resistor (e.g. digitized to be a value between 0 and 256 , depending on force) lies outside the selected min/max sensitivity range, the comparator output will be fully on or fully off, accordingly. If the signal is within the sensitivity range, the comparator output will be scaled proportionally. That is, using speed as an example, if the low sensitivity range is the full speed range of a given blade (for example, 400 to 4000 rpm) will be controlled over the sensitivity range of values from, say, 4 to 40 . If the level signal corresponding to the resistance of the force sensitive resistor is 20 coming out of an analog/digital converter (i.e., within the selected range), the output of comparator 100 will be a signal level sufficient to produce a speed of 2400 rpm (i.e. proportional to the signal output of the force sensitive resistor at a rate of 100 rpm per single level —400 rpm +(100 rpm/level) (20 levels)). The maximum values of each range represent the minimum amount of force necessary to activate the blade at its lowest speed (the resistance of the force sensitive resistor is inversely proportional to the force applied). Any foot switch output corresponding to a force below this minimum amount of force on the foot switch has no effect and the blades do not turn. As more force is applied to the foot switch, the digitized output signal decreases and the rpm increases until level 4 when the speed will be at its maximum. At this minimum value of each range one reaches the maximum amount of force beyond which variability is not produced. An amount of force above this level does not change the maximum speed of the blade.

Because system 10 is microprocessor controlled, numerous programs may be tailored for each user of a group via a menu driven selection process. For example, if the "Help" button 53 is held depressed, a menu prompt "Select Setup Name" appears on display 58 and then the word "Default" is displayed. Pressing the "increase" and "decrease" buttons 56a and 56b enables the user to scroll through four user name setups: Default, Setup 1, Setup 2 and Setup 3. Pressing the "Audio" button 57 will cause the system to accept one of these choices and continue to the next menu item: "Record Setting OFF "or "Record Setting ON". Scrolling (via button 56a/b) through the menu at this point and accepting (via button 53) the selection enables the user to save in memory various user adjustable functions or not. Numerous other programming operations may be designed into the system to, for example, enable or disable any handpiece controls, edit any setup, replace the display "Setup 1" with the name of a particular doctor, etc.

It will be understood by those skilled in the art that numerous improvements and modifications may be made to the invention disclosed herein without departing from the spirit and scope thereof.

What is claimed is:

1. A foot switch for a surgical cutting apparatus comprising:

a base plate;

a plurality of force sensitive resistor means operatively affixed to said base plate, said force sensitive resistor means arranged in a predetermined pattern and for producing a signal having a characteristic dependent upon the force with which said force sensitive resistor means is affected;

connecting means for operatively connecting said force sensitive resistor means to the surgical cutting apparatus;

a flexible, integral, aperture-less cover adapted to receive and enclose at least said base plate and force sensitive resistor means, said cover comprising a plurality of predetermined function-activating areas in overlying alignment with said force sensitive resistor means, said predetermined areas being sufficiently flexible to enable selected ones of said areas to be pressed with varying selected amounts of pressure to apply variable force to a corresponding underlying one of said force sensitive resistor means to activate a predetermined function associated therewith.

2. A foot switch according to claim 1 further comprising a printed circuit membrane wherein said plurality of force sensitive resistor means are arranged in said predetermined pattern on a printed circuit membrane.

3. A foot switch according to claim 1 wherein a void exists between said force sensitive resistor means and said cover further comprising a flexible member situated in said void, said member adapted to transmit force applied to selected ones of said predetermined function-activating areas to associated ones of said underlying force sensitive resistors means.

4. A foot switch according to claim 3 further comprising a plurality of raised areas coincident with selected ones of said predetermined function-activating areas, said raised areas for causing a user to apply force to said raised areas from a first level above a supporting floor surface, said first level being higher than adjacent non-raised areas of said cover.

5. A foot switch according to claim 1 wherein said cover is arcuate in plan view.

6. A foot switch according to claim 5 wherein said cover is inclined in that it extends a greater distance from a supporting floor surface along the outside arc of said plan view than along the inside arc thereof.

7. A foot switch according to claim 5 further comprising said inside arc being adjacent said supporting floor surface in order for a user to position the heel of a foot on said floor surface within the inside arc and activate said predetermined function-activating areas with the sole of said foot.

8. A foot switch according to claim 1 further comprising an elastomeric insert interposed, and adapted to occupy space, between said cover and said base plate.

9. A foot switch comprising:
  (a) an integral, sealed planar housing having a substantially arcuate configuration within the plane of said housing;
  (b) first control means at one end of said housing;
  (c) second control means at the other end of said housing;
  (d) third control means approximately equidistant from said first and second control means;
  (e) fourth control means approximately equidistant from said first and third control means;
  (f) fifth control means approximately equidistant from said second and third control means;
  (g) said fourth and fifth control means raised above the body of said housing relative to said first, second and third control means.

10. A foot switch for a surgical apparatus comprising:

a plurality of force sensitive transducer means arranged in a predetermined pattern and for producing a signal having a characteristic proportional to the force with which said force sensitive transducer means is affected;

connecting means for operatively connecting said force sensitive transducer means to the surgical apparatus in order to activate a predetermined function associated with a corresponding force sensitive transducer means;

a flexible, integral, aperture-less cover adapted to receive and enclose said force sensitive transducer means, said cover comprising a plurality of predetermined function-activating areas in overlying alignment with said force sensitive transducer means, said predetermined areas adapted to enable the transfer of variable amounts of force through selected ones of said areas to a corresponding underlying one of said force sensitive transducer means to activate said predetermined function associated therewith.

* * * * *